US011273114B2

(12) United States Patent
Guo

(10) Patent No.: US 11,273,114 B2
(45) Date of Patent: Mar. 15, 2022

(54) COMPOUND ADDITIVE HAVING BIOLOGICAL ACTIVATION FUNCTION, PREPARATION METHOD THEREFOR AND USE THEREOF

(71) Applicants: Lei Guo, Beijing (CN); Cheng Li, Beijing (CN); SCLNOW BIOTECHNOLOGY CO., LTD, Beijing (CN)

(72) Inventor: Lei Guo, Beijing (CN)

(73) Assignees: Lei Guo, Beijing (CN); Cheng Li, Beijing (CN); SCLNOW BIOTECHNOLOGY GROUP CO., LTD, Beijing (CN)

( * ) Notice: Subject to any disclaimer, the term of this patent is extended or adjusted under 35 U.S.C. 154(b) by 221 days.

(21) Appl. No.: 16/473,209

(22) PCT Filed: May 3, 2017

(86) PCT No.: PCT/CN2017/082790
§ 371 (c)(1),
(2) Date: Jun. 24, 2019

(87) PCT Pub. No.: WO2018/120562
PCT Pub. Date: Jul. 5, 2018

(65) Prior Publication Data
US 2020/0093726 A1    Mar. 26, 2020

(30) Foreign Application Priority Data
Dec. 28, 2016   (CN) .......................... 201611234340.6

(51) Int. Cl.
| C12N 5/0775 | (2010.01) |
| C12N 5/00 | (2006.01) |
| A61K 8/64 | (2006.01) |
| A61Q 19/08 | (2006.01) |

(52) U.S. Cl.
CPC ............... *A61K 8/64* (2013.01); *A61Q 19/08* (2013.01); *C12N 5/0031* (2013.01); *C12N 5/0665* (2013.01); *C12N 2501/105* (2013.01); *C12N 2501/11* (2013.01); *C12N 2501/115* (2013.01); *C12N 2501/135* (2013.01); *C12N 2501/165* (2013.01); *C12N 2501/998* (2013.01)

(58) Field of Classification Search
None
See application file for complete search history.

(56) References Cited

U.S. PATENT DOCUMENTS

| 7,348,409 | B2 | 3/2008 | Garbe et al. | |
| 2010/0159025 | A1* | 6/2010 | Kramer | A61P 25/00 424/583 |
| 2014/0134732 | A1* | 5/2014 | Ashton | C12N 5/0619 435/377 |
| 2014/0170693 | A1* | 6/2014 | Ince | C12N 5/0693 435/29 |
| 2018/0163177 | A1* | 6/2018 | Lo | C12N 5/0665 |

FOREIGN PATENT DOCUMENTS

| CN | 1882837 A | 12/2006 | |
| CN | 101248192 A | 8/2008 | |
| CN | 102120033 A | 7/2011 | |
| WO | WO 02/05828 A1 | 1/2002 | |
| WO | WO 2009/136033 A2 | 11/2009 | |
| WO | WO 2010/008573 A2 | 1/2010 | |
| WO | WO-2010008573 A2 * | 1/2010 | .............. A61K 9/19 |
| WO | WO 2011/036174 A1 | 3/2011 | |
| WO | WO 2014/207181 A1 | 12/2014 | |

OTHER PUBLICATIONS

Wang et al. "Immobilized metal affinity chromatography and human serum proteomics." Journal of Chromatography B 934 (2013): 26-33. (Year: 2013).*
Eisenman et al. "Protein and water of serum and cells of human blood, with a note on the measurement of red blood cell volume." Journal of Biological Chemistry 116.1 (1936): 33-45. (Year: 1936).*
Ge et al. "Secretome of olfactory mucosa mesenchymal stem cell, a multiple potential stem cell." Stem Cells International 2016 (published Feb. 1, 2016). (Year: 2016).*
Rackham et al. "Mesenchymal stromal cell secretory factors induce sustained improvements in islet function pre-and post-transplantation." Cytotherapy 20.12 (2018): 1427-1436. (Year: 2018).*
Skalnikova "Proteomic techniques for characterisation of mesenchymal stem cell secretome." Biochimie 95.12 (2013): 2196-2211. (Year: 2013).*
Rhee et al. "Mesenchymal stem cell-mediated effects of tumor support or suppression." International Journal of Molecular Sciences 16.12 (2015): 30015-30033. (Year: 2015).*
Partial English translation of CN 102120033 A claims.

* cited by examiner

*Primary Examiner* — Emily A Cordas
(74) *Attorney, Agent, or Firm* — Lewis Roca Rothberger Christie LLP

(57) ABSTRACT

A compound additive having a biological activation function. The compound additive contains water or phosphate buffer, and multiple proteins and various factors dissolved therein. The compound additive can be added into a culture medium for cell cultivation, and can also be directly used or added into a skin repair product or a cosmetic product so as to achieve certain skin repair and cosmetic effects.

2 Claims, 1 Drawing Sheet

1A  1B  1C

COMPOUND ADDITIVE HAVING BIOLOGICAL ACTIVATION FUNCTION, PREPARATION METHOD THEREFOR AND USE THEREOF

CROSS-REFERENCE TO RELATED APPLICATION(S)

This application is a National Phase Patent Application of International Patent Application Number PCT/CN2017/082790, filed on May 3, 2017, which claims priority of Chinese Patent Application No. 201611234340.6, filed Dec. 28, 2016. The entire contents of both of which are incorporated herein by reference.

TECHNICAL FIELD

The present invention relates to the field of stem cell culture and medicine. Particularly, the present invention relates to a composite additive having a biologically activating function, which can be used for cell culture, skin repair and beautifying, and the like.

BACKGROUND OF THE INVENTION

Mesenchymal stem cells (MSCs) are ubiquitous in many tissues and organs of human body, and have multi-directional differentiation potential. They have functions of stimulating tissue regeneration, and regulating immunity, and have a broad application prospect in the field of cell therapy.

Active proteins secreted by MSCs have an immunomodulatory activity both in vitro and in vivo, and can inhibit graft rejection in vivo and prolong graft survival time. It has been found that active proteins secreted by MSCs play an important role in improving and repairing functions of target organs and tissues, resisting inflammation and apoptosis, regulating immunity, and the like. Meanwhile, it has also been reported that active proteins secreted by MSCs have efficacies of maintaining beauty, resisting aging, and making people younger.

SUMMARY OF THE INVENTION

Based on studies on proteins secreted by stem cells, the present invention provides a composite additive which can be used for stem cells culture, skin repair and skin beautifying.

Therefore, one purpose of the present invention is to provide a composite additive having a biologically activating function, which comprises water, proteins and various factors. The composite additive can be added to a cell culture medium for culturing cells, and can also be used directly or added to skin repair products or skin cosmetic products to achieve skin repair and skin cosmetic effects.

Technical solutions provided by the present invention are as follows.

In one aspect, the present invention provides a composite additive having a biologically activating function, the composite additive comprising water or phosphate buffer; and following ingredients dissolved therein:
human serum albumin;
dermcidin;
apolipoprotein A;
haptoglobin;
beta-globin;
annexin A1;
transthyretin;
transgelin;
human platelet factor 4;
human platelet basic protein;
platelet-derived growth factor-AB (PDGF-AB);
platelet-derived growth factor-BB (PDGF-BB);
insulin-like growth factor-1 (IGF-1);
epidermal growth factor (EGF);
vascular endothelial growth factor (VEGF);
fibroblast growth factor-2 (FGF-2).

Preferably, the composite additive comprises water or 0.005-0.01 M phosphate buffer; and following ingredients dissolved therein:
500-1000 μg/mL human serum albumin;
100-200 μg/mL dermcidin;
100-200 μg/mL apolipoprotein A;
200-500 μg/mL haptoglobin;
200-500 μg/mL beta-globin;
100-200 μg/mL annexin A1;
200-500 μg/mL transthyretin;
20-200 μg/mL transgelin;
200-500 μg/mL human platelet factor 4;
50-200 μg/mL human platelet basic protein;
20-50 ng/ml platelet-derived growth factor-AB (PDGF-AB);
20-50 ng/ml platelet-derived growth factor-BB (PDGF-BB);
10-20 ng/ml insulin-like growth factor-1 (IGF-1);
200-500 μg/ml epidermal growth factor (EGF);
100-200 μg/ml vascular endothelial growth factor (VEGF);
100-500 ng/ml fibroblast growth factor-2 (FGF-2).

More preferably, the composite additive comprises water or 0.0067 M phosphate buffer; and following ingredients dissolved therein:
750 μg/mL human serum albumin;
150 μg/mL dermcidin;
150 μg/mL apolipoprotein A;
250 μg/mL haptoglobin;
250 μg/mL beta-globin;
150 μg/mL annexin A1;
300 μg/mL transthyretin;
100 μg/mL transgelin;
500 μg/mL human platelet factor 4;
100 μg/mL human platelet basic protein;
20 ng/ml platelet-derived growth factor-AB (PDGF-AB);
20 ng/ml platelet-derived growth factor-BB (PDGF-BB);
10 ng/ml insulin-like growth factor-1 (IGF-1);
200 μg/ml epidermal growth factor (EGF);
200 μg/ml vascular endothelial growth factor (VEGF);
200 ng/ml fibroblast growth factor-2 (FGF-2).

In another aspect, the present invention provides a method for preparing the above composite additive.

The method includes dissolving the ingredients in the water or the phosphate buffer. The ingredients are all products that can be obtained through conventional purchase, or the phosphate buffer can be prepared.

The composite additive provided in the present invention can be added to a cell culture medium.

Therefore, in yet another aspect, the present invention also provides a cell culture medium comprising the composite additive.

According to some specific embodiments of the present invention, the cell culture medium comprises: 0.1 parts by volume of β-mercaptoethanol, 1 part by volume of aqueous solution of non-essential amino acids (11140, Gibco), 94 parts by volume of a-MEM/DMEM-F12 and 5 parts by volume of the composite additive.

The composite additive of the present invention or the cell culture medium comprising the same can be used in long-term expending and culturing stem cells in vitro. The stem cells are particularly umbilical cord mesenchymal stem cells isolated from an umbilical cord of a newborn.

Therefore, in still another aspect, the present invention also provides a use of the composite additive or the cell culture medium comprising the same in manufacturing a media for culturing stem cells.

The stem cells are isolated from tissue or organ of a mammal, such as human, which is one or more selected from the group consisting of bone marrow, umbilical cord and fat; preferably, the stem cells are umbilical cord mesenchymal stem cells of mammalian origin; more preferably, the stem cells are umbilical cord mesenchymal stem cells of human origin; further preferably, the stem cells are human umbilical cord mesenchymal stem cells isolated from a fresh umbilical cord tissue of a healthy newborn delivered naturally or by cesarean section.

The composite additive provided by the present invention can also be added to a skin cosmetic composition.

Therefore, in yet still another aspect, the present invention also provides a skin cosmetic composition comprising the composite additive.

The composite additive provided by the present invention or the skin cosmetic composition comprising the same can be well absorbed by skin and can promote cutaneous circulation. Especially, when added to a lotion or an emulsion, it can improve the fusion and absorption of the lotion and emulsion, thereby providing a good cosmetic effect. The way of using the composite additive or the skin cosmetic composition comprising the same is to add it into a cosmetic base. A water-soluble base such as glycerin or emulsion is recommended in consideration of the solubility of the composite additive.

Therefore, in another aspect, the present invention also provides a use of the composite additive or the skin cosmetic composition comprising the same in manufacturing a skin cosmetic product.

The composite additive provided by the present invention can also be added to a skin repair composition.

Therefore, in yet still another aspect, the present invention also provides a skin repair composition comprising the composite additive.

The composite additive provided by the present invention or the skin repair composition comprising the same can not only relieve itching and pain at a mosquito bite, sterilize and disinfect the mosquito bite, but also repair the skin where a mosquito bites, and therefore infection caused by scratching is avoided.

Therefore, in still another aspect, the present invention also provides a use of the composite additive or the skin repair composition comprising the same in manufacturing a skin repair product.

On the basis of the properties and effects of the composite additive provided by the present invention, the present invention also provides a method for beautifying skin, the method including administering to a subject in need thereof a suitable amount of the composite additive or the skin cosmetic composition comprising the same. What's more, the present invention also provides a method for repairing skin, the method including administering to a subject in need thereof a suitable amount of the composite additive or the skin repair composition comprising the same. The subject is preferably a human.

Specifically, the composite additive provided by the present invention has not only safety, non-toxicity and other properties, but also a significant biologically activating function. For example, in case the composite additive of the present invention is added to a cell culture medium for culturing stem cells, it enables the stem cells to proliferate normally while also maintains the stability and pluripotency of the stem cells. In addition, with the significant biologically activating function, the composite additive itself can be used as a skin cosmetic product or a skin repair product. When the composite additive is used as a skin cosmetic product, it will not cause skin irritation, but has anti-wrinkle and anti-aging effects and leaves skin crystal and clear at the same time; while when the composite additive is used as a skin repair product, it plays a role in relieving itching and pain, sterilizing, disinfecting, repairing, preventing infection and the like. Based on the special functions of the composite additive, it can not only be used alone, but also be added to cosmetics or skin repair products as an additive. A product obtained by adding the composite additive therein has a good permeation in vitro and can function through the skin, and also has the above-mentioned cosmetic or repair functions. Therefore, the composite additive provided by the present invention has a very wide range of applications.

BRIEF DESCRIPTION OF THE DRAWINGS

Hereinafter, embodiments of the present invention will be described with reference to the accompanying drawings in detail, in which.

DETAILED DESCRIPTION OF PREFERRED EMBODIMENTS

The present invention will be further described in detail in combination with the specific embodiments hereinafter. The embodiments provided are only used to illustrate the present invention, rather than limiting the scope of the present invention in any way.

Experimental methods in the following examples, if no any other special instruction is provided, are all conducted under conventional conditions or the conditions recommended by the instrument or reagent supplier. Materials used in the following examples, if no source of purchase is provided, are conventional products that can be commercially available.

EXAMPLE 1: PREPARATION OF THE COMPOSITE ADDITIVE AND CULTURE OF STEM CELLS

Preparation of the Composite Additive:

75 mg human serum albumin, 15 mg dermcidin, 15 mg apolipoprotein A, 25 mg haptoglobin, 25 mg beta-globin, 15 mg annexin A1, 30 mg transthyretin, 10 mg transgelin, 50 mg human platelet factor 4, 10 mg human platelet basic protein, 2 μg platelet-derived growth factor-AB (PDGF-AB), 2 μg platelet-derived growth factor-BB (PDGF-BB), 1 μg insulin-like growth factor-1 (IGF-1), 20 μg fibroblast growth factor-2 (FGF-2), 20 ng epidermal growth factor (EGF), and 20 ng vascular endothelial growth factor (VEGF) that were accurately weighed or as a liquid measured were added into 75 ml sterile water, and the final volume was set to be 100 mL. The obtained composite additive was stored at 4° C.

Preparation of a Serum-Free Medium:

Composition: 0.1 parts by volume of β-mercaptoethanol, 1 part by volume of aqueous solution of non-essential amino acids (11140, Gibco), 94 parts by volume of a-MEM/DMEM-F12 and 5 parts by volume of the composite additive.

The β-mercaptoethanol, the aqueous solution of non-essential amino acids and the a-MEM/DMEM-F12 were formulated into a premixed solution, and then the composite additive was mixed with the premixed solution.

Figure 1:
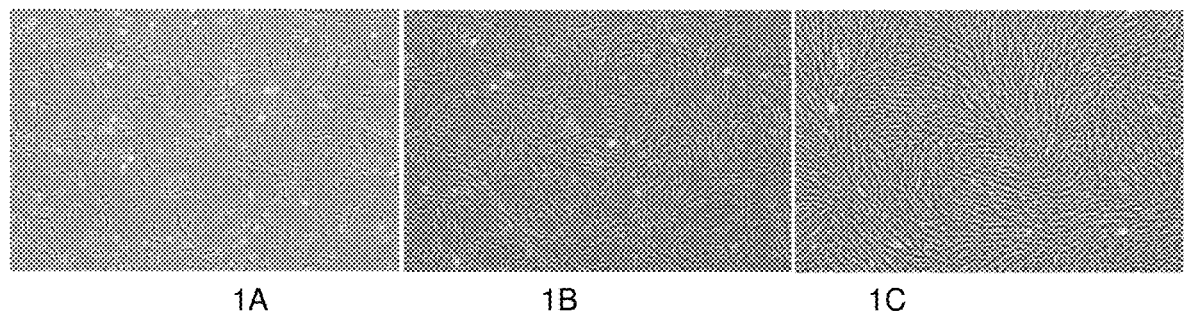
FIG. 1 shows pictures of umbilical cord mesenchymal stem cells cultured in a serum-free medium formulated with the composite additive provided by the present invention, in which panel 1A shows cellular morphology of cells 2 hours after inoculation, panel 1B shows cellular morphology of cells 24 hours after inoculation, and panel 1C shows cellular morphology of cells 48 hours after inoculation.

Culture of Cells:

In a biosafety cabinet, the third generation human umbilical cord mesenchymal stem cells (hUC-MSCs) isolated from Wharton's jelly tissue of umbilical cord of a newborn delivered naturally were inoculated into a T175 cell culture flask at a density of $2 \times 10^4$ cells/cm$^2$, then the flask was transferred to a constant temperature incubator at 37° C., 5% $CO_2$ after 15 ml of the serum-free medium was added therein. The cells were observed to have adhered 2 hours after inoculation. Cultured continuously, the cells were observed to have completely adhered 4 hours after inoculation, and 24 hours after inoculation, it was observed that the hUC-MSCs appeared as spindle-shape and gathered in whorls spreading much more, and the cells were bright, and 40-60% confluence was reached. Subsequent observation 48 hours after inoculation showed that the hUC-MSCs were bright and more than 90% confluence was reached. Then the cells were digested by trypsin, collected and cryopreserved. The results were shown in FIG. 1.

EXAMPLE 2: PREPARATION OF A CREAM CONTAINING THE COMPOSITE ADDITIVE AND EFFECTS THEREOF

The composite additive was prepared with the same method as described in Example 1.

Preparation of a Cream Containing the Composite Additive:

Composition: 20 g stearic acid, 10 g liquid paraffin, 10 g glycerin, 2 g triethanolamine, 0.1 g ethyl Hydroxybenzoate, 3 g laurocapram, 10 ml of the composite additive and an appropriate amount of distilled water; the total amount of the cream is 100 g. In the cream, glycerin, triethanolamine, the composite additive and the distilled water serve as aqueous phase, and the rest serve as oil phase.

The composite additive, the stearic acid, the glycerin, the liquid paraffin, the ethyl Hydroxybenzoate and the laurocapram were added to a beaker, and stirred to dissolve completely in a water bath at 100° C., and then the triethanolamine was added into the beaker, the obtained mixture was stirred till it condensed to obtain a white cream.

Stability Test:

1. Centrifugal Test 10 g of the cream prepared above was taken and added into a graduated centrifuge tube, and then centrifuged at 2500 r/m in for 30 min.

2. Heat Resistance Test 10 g of the cream prepared above was taken and added into a graduated centrifuge tube, and the tube was then placed in a water bath with a constant temperature of 55° C. for 6 hours.

3. Cold Resistance Test 10 g of the cream prepared above was taken and added into a graduated centrifuge tube, and the tube was then placed in a refrigerator at −20° C. for 24 hours.

4. In Vitro Drug Release Test

A SD rat was sacrificed and its abdominal hair was removed. Subsequently, its abdominal skin was bluntly dissected and subcutaneous fat was removed mechanically. The obtained rat skin was washed with physiological saline, and stored at −20° C. until use. The rat skin was thawed before use and washed with physiological saline.

A modified Franz diffusion cell was used as the device of this experiment, in which the upper cell that served as a donor cell was a tube of 1.6 cm internal diameter, and the lower cell that served as a receptor cell was a stoppered conical flask. 100 ml of physiological saline was added to the receptor cell as receiving liquid; and the rat skin was fixed at the lower end of the donor cell with the side of stratum corneum upward. The cream was uniformly applied to the stratum corneum, followed by filling 10 ml of physiological saline into the donor cell. Afterwards, the donor cell was fixed on the receptor cell after being sealed. An agitator was placed in the receptor cell and the side of the skin dermis fully contacted with the receiving liquid, ensuring that no air bubble existed. Finally, that whole system was placed on a heated magnetic stirrer and stirred at 37° C. at a speed of 300 r/m in. The effective diffusion area of the device was 2.0 cm$^2$. The liquid in the receptor cell was completely discharged at 3, 4, 5, 6, 7, 8, 9, and 10 hours respectively, followed by adding the blank receiving liquid thereto. The receiving liquid obtained at each time point was filtered through a 0.45 μm filter, and the amount of protein diffused in the receiving liquid was calculated using a standard curve, and the percentage of cumulative diffusion was determined as compared with the total protein amount.

In an in vitro drug release test, it is generally believed that the process of a drug passing through skin is a passive diffusion process, which is commonly described by Fick's law of diffusion. The skin is regarded as a homogeneous membrane and when the drug diffuses through the skin to reach a steady state, the steady-state permeation rate is expressed by the formula:

$$J_s=(dQt/S)/dt=P_s(C_d-C_i)/s$$

In the formula, $J_s$: drug permeation rate, $\mu g \cdot cm^{-2} \cdot h^{-1}$;
S: effective diffusion area (cm$^2$);
T: time (h);
$P_s$: permeability coefficient;
$C_d$: concentration of the drug in the donor cell (μg).

However, in this test, the concentration of the drug in the donor cell was far greater than that in the receptor cell, so the above formula had been rewritten as follows:

$$J_s=(dQt/S)/dt=P_sC_d.$$

The sampling time was taken as the horizontal coordinate and the percentage of cumulative diffusion as the vertical coordinate, and a sampling time-percentage of cumulative diffusion curve was plotted.

Figure 2:
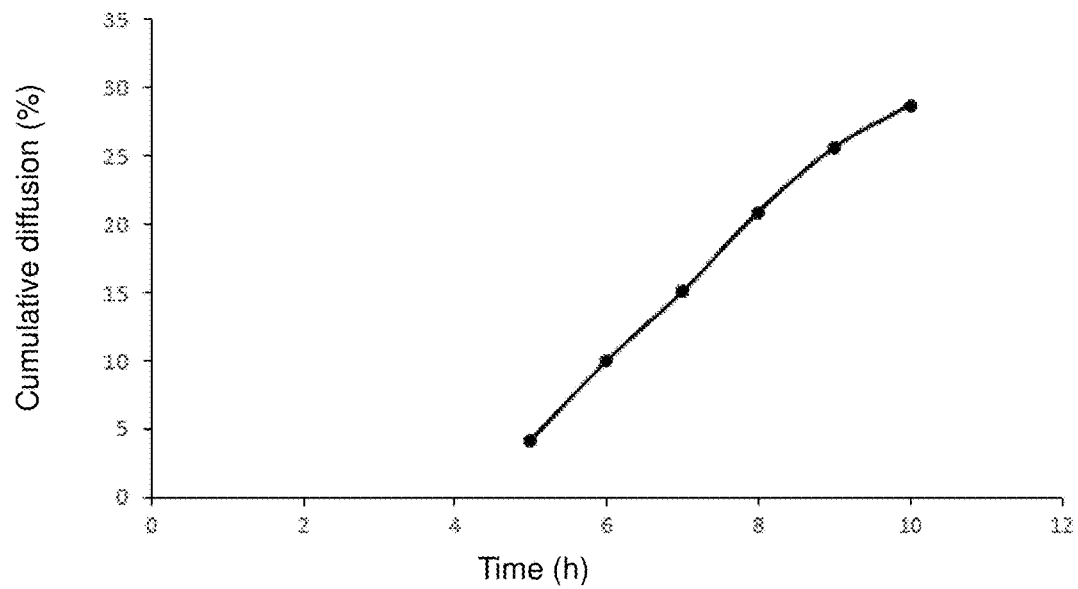
FIG. 2 shows a permeability curve of a cream prepared with the composite additive of the invention over time.

Results:

The cream was white, smooth and even, and the base of it was W/O. The various cytokines and proteins comprised in the composite additive were dissolved in the base completely by the emulsification reaction between stearic acid and triethanolamine. In addition, the obtained cream had a stable quality and no stratification was observed in the centrifugal test, heat resistance test and cold resistance test. However, the cream is not recommended to expose to high heat given that most of the active ingredients in the composite additive were proteins that can be destroyed easily by high temperature. It was found that the cream containing the composite additive had a good permeation performance in vitro and could function through the skin. The results were shown in FIG. 2.

EXAMPLE 3: OBSERVATION OF THERAPEUTIC EFFECT OF THE COMPOSITE ADDITIVE ON MOSQUITO BITES

1. Experimental Material: The Composite Additive Prepared in Example 1.
2. Diagnostic Criteria for Bites: All Cases
(1) are bit by mosquitoes or other insects; and
(2) feel intense local itching after being bitten.
3. Criteria for Therapeutic Efficacy
Cured: systemic and local symptoms disappear, and symptoms such as skin redness and swelling, fever, pain and itching subside.
Effective: systemic and local symptoms are relieved and swelling subsides.
Ineffective: systemic and local symptoms are not controlled or even aggravated.
4. Experimental Method
50 patients with mosquito bites were selected without age or sex restrictions. Upon the skin was bit by a mosquito, the composite additive was evenly applied to the red and swollen area twice a day. The dosage applied was adjusted according to the size of the area and therapeutic effect was observed.
5. Therapeutic Effect (Shown by Therapeutic Efficacy)
It was observed that 23 cases were cured, and the composite additive showed effective in 25 cases while ineffective in 2 cases. The overall effective rate was 96%.

EXAMPLE 4: OBSERVATION OF COSMETIC AND REPAIR EFFECTS OF THE COMPOSITE ADDITIVE ON SKIN

1. Experimental Material: The Composite Additive Prepared in Example 1.
2. Criteria for Therapeutic Efficacy (0-10 Scores)
Unobvious effect: 0-3 scores;
General effect: 4-6 scores;
Remarkable effect: 7-10 scores.
3. Experimental Method:
60 subjects were selected without age or sex restrictions, and then randomly divided into experimental group and placebo group. As for the experimental group: every day the subjects applied the composite additive of the present invention onto their face after cleaning the face in the morning and evening, with continue application for 30 days. As for the placebo group: every day the subjects applied pure water onto their face after cleaning the face in the morning and evening, with continue application for 30 days.

4. Therapeutic Effect (Shown by Scores of the Therapeutic Efficacy)
The experimental group: 8.0±0.8.
The placebo group: 2.6±0.9.
From the results it can be seen that the composite additive had significant cosmetic effect as highly appraised by the subjects.
5. Specific Example:
Subject Cao was a female 50 years old, who had deep crow's feet, large pouches and obvious dark circles before test. After applying the composite additive of the present invention, she found the crow's feet became lighter, the pouches smaller and the dark circles less obvious.

The above description for the embodiments of the present invention is not intended to limit the present invention, and those skilled in the art can make various changes and variations according to the present invention, which are within the protection scope of the present invention without departing from the spirit of the same.

What is claimed is:
1. A method for manufacturing a medium for culturing stem cells, the method comprising
preparing a premixed solution utilizing 0.1 parts by volume of β-mercaptoethanol, 1 part by volume of aqueous solution of non-essential amino acids, and 94 parts by volume of a-Minimum Essential Medium (a-MEM) or Dulbecco's Modified Eagle Medium nutrient mixture F-12 (DMEM-F12); and
mixing the premixed solution and 5 parts by volume of a composite additive; and
wherein the composite additive comprises water or 0.0067 M phosphate buffer; and following ingredients dissolved therein:
750 μg/mL human serum albumin;
150 μg/mL dermcidin;
150 μg/mL apolipoprotein A;
250 μg/mL haptoglobin;
250 μg/mL beta-globin;
150 μg/mL annexin A1;
300 μg/mL transthyretin;
100 μg/mL transgelin;
500 μg/mL human platelet factor 4;
100 μg/mL human platelet basic protein;
20 ng/ml platelet-derived growth factor-AB;
20 ng/ml platelet-derived growth factor-BB;
10 ng/ml insulin-like growth factor-1;
200 pg/ml epidermal growth factor;
200 pg/ml vascular endothelial growth factor; and
200 ng/ml fibroblast growth factor-2.
2. The method according to claim 1, wherein the stem cells are human umbilical cord mesenchymal stem cells isolated from a fresh umbilical cord tissue of a healthy newborn delivered naturally or by cesarean section.

* * * * *